United States Patent [19]

Hublikar et al.

[11] Patent Number: 4,998,825
[45] Date of Patent: Mar. 12, 1991

[54] TIRE CORD THERMAL ANALYSIS TESTING DEVICE AND METHOD

[75] Inventors: Sudhendra V. Hublikar, Olmsted Falls; Leonard G. Kinaitis, Hinckley, both of Ohio

[73] Assignee: The Uniroyal Goodrich Tire Company, Akron, Ohio

[21] Appl. No.: 435,729

[22] Filed: Nov. 13, 1989

[51] Int. Cl.⁵ .................... G01B 5/02; G01N 3/08; G01N 3/16
[52] U.S. Cl. .................... 374/50; 33/787; 73/826; 374/55
[58] Field of Search .................... 374/55, 51, 50, 49, 374/46, 14; 73/831, 828; 219/201

[56] References Cited

U.S. PATENT DOCUMENTS

| | | | |
|---|---|---|---|
| 1,327,393 | 1/1920 | Jury | 73/833 X |
| 2,600,923 | 6/1952 | Rogers et al. | 73/833 X |
| 2,660,051 | 11/1953 | Dowling | 374/51 |
| 2,837,915 | 6/1958 | Brown, Jr. et al. | 73/831 |
| 3,075,378 | 1/1963 | Bernard et al. | 374/51 |
| 3,316,757 | 5/1967 | Fletcher et al. | 73/831 |
| 3,934,452 | 1/1976 | Prevorsek et al. | 374/47 |
| 4,019,365 | 4/1977 | Woo | 374/46 |
| 4,073,185 | 2/1978 | Griffin | 73/833 |
| 4,535,636 | 8/1985 | Blackburn et al. | 374/55 X |
| 4,562,743 | 1/1986 | Bonine | 73/828 |
| 4,884,456 | 12/1989 | Meline et al. | 374/55 |

FOREIGN PATENT DOCUMENTS 1299171 12/1972 United Kingdom.

OTHER PUBLICATIONS

*Tire Cord Process Simulation and Evaluation, Kautschuk und Gummi Kunststoffe*, by C. Z. Draves and L. Skolnik, vol. 22, No. 10, pp. 561–565 (1969).

Primary Examiner—Daniel M. Yasich
Attorney, Agent, or Firm—Howard S. Robbins; Reese Taylor; Alan A. Csontos

[57] ABSTRACT

Dimensional change in a tire cord (13) under thermomechanical stress is determined by a device (10) including an oven (12) for receiving and controlling the temperature of a preselected length of the cord (13), grips (14,15) for holding and selectively positioning the entire preselected length of cord (13) within the oven (12), and means (16) including an angular displacement transducer (51) for measuring changes in the preselected length of cord (13). Means (16) may also include weights (52,53) for the selective application of mechanical stress to the material. The steps employed in determining such dimensional change include inserting a length of cord (13) into grips (14,15), positioning the entire length of cord (13) (including the portion of grips (14,15) holding the cord (13)) within oven (12), controlling the temperature of the cord (13) in the oven (12), and measuring changes in the length of cord (13).

13 Claims, 4 Drawing Sheets

TIRE CORD THERMAL ANALYSIS TESTING DEVICE AND METHOD

TECHNICAL FIELD

The present invention relates generally to the determination of a thermomechanical characteristic of materials. More particularly, the present invention relates to the determination of a thermomechanical characteristic of high-strength, synthetic fibers exhibiting thermoelastic properties, such as polyamides and polyesters. More specifically, the present invention relates to a device and method for automatically determining the change of length such fibers undergo during various stages of manufacture.

BACKGROUND ART

It has long been known that the length of thermoplastic fibers such as nylon and polyester change length during curing and related manufacturing processes. When such fibers are incorporated within pneumatic tires as reinforcing or stabilizing cords, successful manufacture requires an accurate allowance for such length change.

In order to quantitatively determine the magnitude of such length change, a single-cord, simulated cure/post-cure inflation (SC/PCI) test device and method was devised which measured the effect on cord length of successive changes in temperature and load. The SC/PCI device is extremely simple in construction; a vertically-oriented cylindrical oven encloses a portion of a similarly oriented length of cord. The top end of the cord is fixed above the cylindrical oven, while a weighted pointer assembly pointing to a linear scale is applied to the bottom of the cord below the oven. A detailed explanation of the SC/PCI test may be found in the article by C.Z. Draves and L. Skolnik, *Tire Cord Process Simulation and Evaluation, Kautschuk Und Gummi Kunststoffe*, Vol. 22, No. 10, pp. 561-565 (1969).

Another method and device utilized to measure cord shrinkage is described in U.K. Patent No. 1,299,171, which is incorporated herein by reference. That manually operated device, made by Testrite Limited of Halifax England and commonly referred to as the Testrite cord shrinkage tester, orients the cord horizontally and, like the SC/PCI test, envisions heating only a portion of the cord to be tested. One end of the cord is fixed while the other end is wrapped around a drum carrying a pointer in front of a partially circular dial having a non-linear scale thereon. An interference fit between the cord and drum causes the drum and pointer to rotate with changes in cord length. The Testrite cord shrinkage tester by design is incapable of applying a significant tensile stress to the test cord and therefore is unable to perform shrinkage measurements requiring mechanical stress such as the SC/PCI.

The SC/PCI and Testrite cord shrinkage tests and implementing devices possess several deleterious features. The extensive processing time (about forty minutes) of the SC/PCI test limits the number of cords that may be tested during manufacture. Also significant are inaccuracies introduced by the devices themselves. One source of inaccuracy is the failure to maintain the cord under test at a uniform temperature which arises from placing only a portion of the cord under test within the oven. In the instance of the Testrite cord shrinkage test additional inaccuracies occur because of the non-linear scale used by the meter. Moreover, the manual operation of both testing devices produces results dependent on individual operator proficiency and requires considerable operator attention.

SUMMARY OF THE INVENTION

It is, therefore, an object of the present invention to provide a device and method for determining dimensional change in a material under thermomechanical stress that is performed rapidly and accurately.

It is another object of the present invention to provide a device and method for determining dimensional change in a material under thermomechanical stress, as above, which minimizes measurement inaccuracies by maintaining the entire length of cord under test at a uniform temperature.

It is still another object of the present invention to provide a device and method for determining dimensional change in a material under thermomechanical stress, as above, which minimizes measurement inaccuracies by measuring dimensional changes linearly.

It is yet another object of the present invention to provide a device and method for determining dimensional change in a material under thermomechanical stress, as above, which is automated to minimize operator induced errors and inaccuracies.

It is a further object of the present invention to provide a device and method for determining dimensional change in a material under thermomechanical stress, as above, which minimizes heat loss and improves energy utilization.

These and other objects and advantages of the present invention over existing prior art forms will become more apparent and fully understood from the following description in conjunction with the accompanying drawings.

In general, a device for determining dimensional change in a material under thermomechanical stress embodying the concept of the present invention includes a chamber for receiving and controlling the temperature of a preselected length of the material, grips for holding and selectively positioning the entire preselected length of the material within the chamber, and means for measuring changes in the preselected length of the material.

In general, a method for determining dimensional change in a material under thermomechanical stress includes the steps of inserting a preselected length of the material into grips, positioning the entire preselected length of the material, including the portion of the grips holding the material, within an oven, controlling the temperature of the preselected length of the material in the oven, and measuring changes in the length of material.

PREFERRED EMBODIMENT FOR CARRYING OUT THE INVENTION

Figure 1:
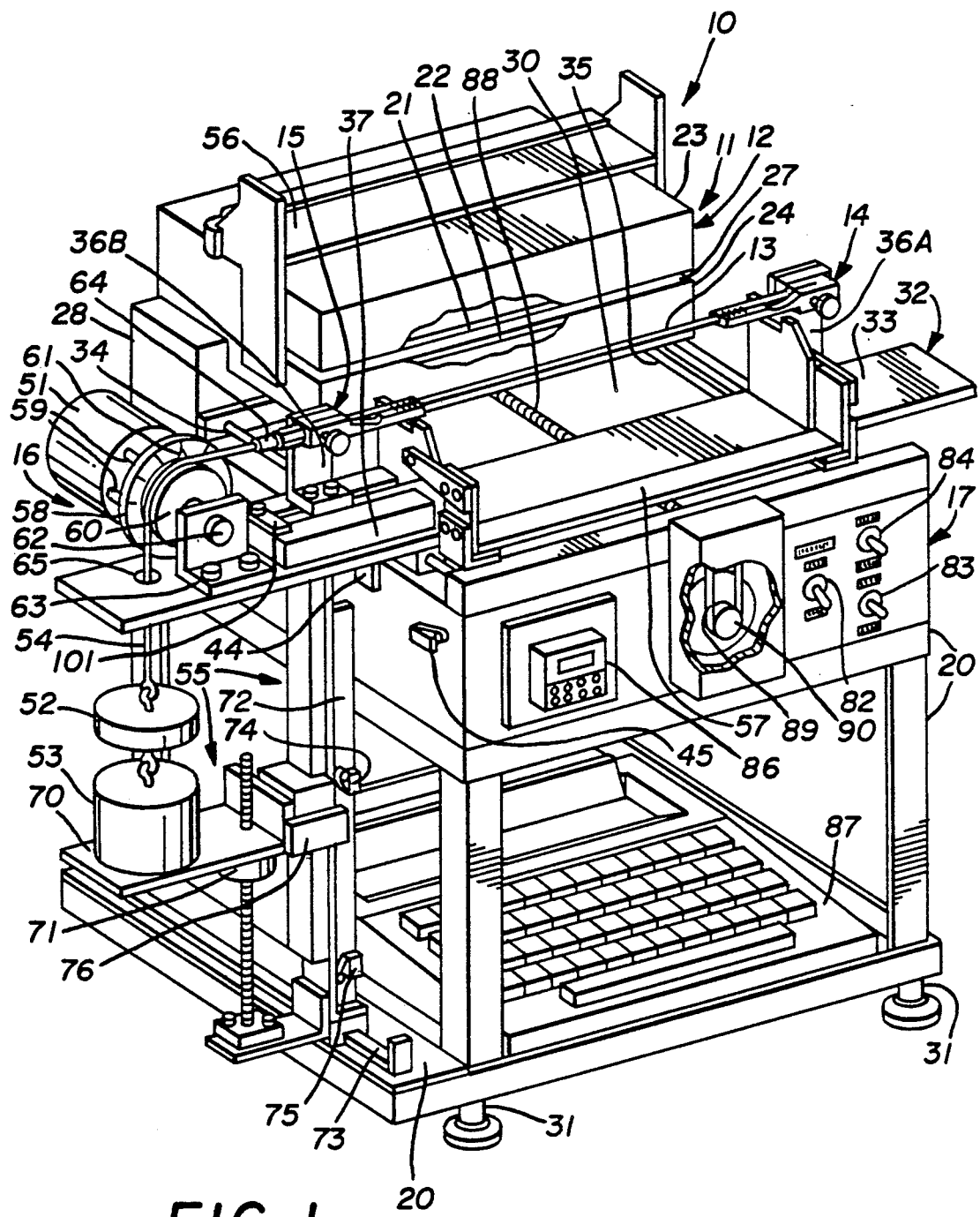
FIG. 1 is a front perspective view of an exemplary device, and embodied exemplary method, for determining dimensional change in a material under thermomechanical stress, in accordance with the concept of the present invention.

FIG. 1 is a front perspective view of an exemplary device, and embodied exemplary method, for determining dimensional change in a material under thermomechanical stress, generally indicated by the reference numeral 10, in accordance with the concept of the present invention. More specifically, the preferred embodiment discloses a device and method primarily intended for use in determining such dimensional changes occurring in tire cords.

Device 10 includes broadly an environmental chamber 11 such as oven 12 to provide a controlled, thermal stress to the test cord, grips 14, 15 to carry the test cord 13, measuring assembly 16 to provide a controlled, mechanical stress to the test cord and measure physical characteristics from which dimensional changes may be calculated, and control 17 to control the operation of device 10, all carried upon a frame 20.

In the present embodiment environmental chamber 11 includes horizontal top and bottom heating elements 21, 22 carried in like-oriented top and bottom insulated enclosures 23, 24, which define oven 12 as having a substantially uniformly heated horizontal heating cavity 27, all similar to that disclosed in the Testrite U.K. Patent. Oven 12 is supported by a vertical extension 28 to a control housing 30, which in turn is carried atop substantially cubic frame 20, the latter optionally including leveling feet 31.

A carriage 32 is positioned atop control housing 30 for allowing test cord 13 secured between grips 14 and 15 to slidably engage and disengage heating cavity 27 by moving inwardly and outwardly with respect to heating cavity 27. Carriage 32 includes a horizontal platform 33, slides 34, 35, and a conventional drive screw 88 driven through belt 89 by motor 90, such as a Model 715 Instrument Motor from Bodine Electric Company of Chicago Ilinois.

Upon command from control 17, motor 90 drives carriage 32 and all that is supports inward to or outward from heating cavity 27 until actuator 44 engages one of two switches 45 (one shown). In the in position the entire test cord 13 is emersed within the controlled, uniform temperature field of heating cavity 27; in the out position test cord 13 is outside heating cavity 27, as shown in FIG. 1.

Grip 14 is mounted to vertical bracket 36A which is in turn fixedly secured to one end of platform 33. Grip 15 is mounted to vertical bracket 36B which is in turn laterally slidably secured to a channel block 37 fixedly mounted upon platform 33, thereby facilitating free lateral motion of grip 15.

Figure 2:
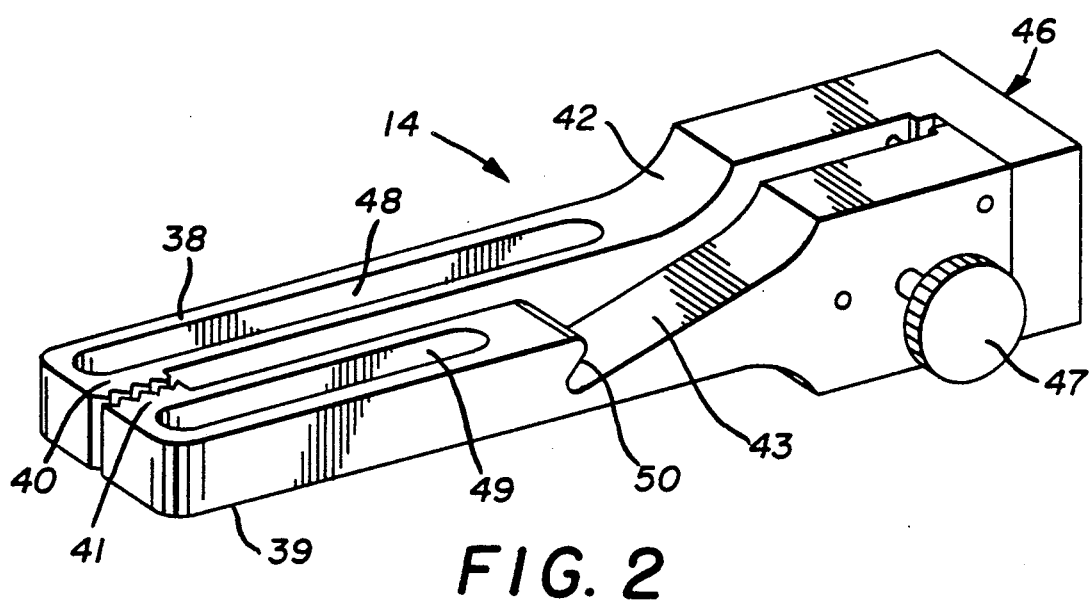
FIG. 2 is a front perspective view of one of the exemplary grips shown in FIG. 1 for holding the test material.

FIG. 2 presents an enlarged front perspective of grip 14 where it can be best seen that the overall shape of grip 14 is that of a bifurcated, substantially rectangular block with two parallel legs 38, 39 in spaced relation. Legs 38, 39 each have at one end thereof a dog-leg jaw 40, 41 with serrated teeth for firmly grasping one end of test cord 13, and at the opposite end shoulders 42, 43 tapering out to the full height of a pinch block assembly 46. Pinch block assembly 46 includes a threaded thumb screw 47 which when rotated clockwise pulls leg 39 into leg 40 until jaws 40 and 41 are in tight engagement. As seen in FIG. 1, grip 15 is a mirror image of grip 14 in every respect except its operative connection to measuring assembly 16, as discussed below.

Several features of grips 14, 15 are intended to allow the entire length of cord 13 under test to fit within heating cavity 27. First, the height of legs 38, 39 must be less than that of heating cavity 27. Also, the gap between legs 38 and 39, selected in major part by the length of dog-leg jaws 40, 41, must be sufficiently great to allow the tail of the test cord that extends beyond jaws 40, 41 to fit therebetween. Finally, an offset 50 may be formed in the top of leg 39 to which shoulder 43 is joined. While offset 50 will primarily facilitate installation of test cord 13 by securing test cord 13 before the jaws have been closed, it will also help insure that the tail of test cord 13 remains clear of the heating cavity 27.

A number of improvements to prior art test cord anchors may now be appreciated. First, by furnishing a grip whose configuration permits the entire length of cord under test to fit within heating cavity 27, variations in the temperature gradient of the test cord, a source of major inaccuracies in prior art measurements is at least substantially reduced. Furthermore, by selecting grips 14, 15 to be made from a material having low heat capacity, such as stainless steel grade 303 rather than conventional aluminum, and by minimizing their mass by cutting cylindrical notches 48, 49 in legs 38, 39, respectively, device 10 requires less energy to operate, and is more efficient and less subject to thermal variations, particularly when changing test cords.

In a further effort to minimize heat loss, energy usage and the time required to reach temperature stability between tests of different test cords, oven 12 may be provided with retractable heat shields to act as closures to the open portions of heating cavity 27 through which test cord 13 is inserted. Heat shields 56, 57 both may be longitudinal doors made of suitable heat insulative material that pivotally engage the open sides and front of heating cavity 27. Heat shield 56 may be pivotally connected to oven 12 such that whenever test cord 13 is outside oven 12, heat shield 56 drops into place. (Although test cord 13 is illustrated in FIG. 1 outside heating cavity 27, heat shield 56 is shown in its retracted position to allow a full view of heating cavity 27.) Heat shield 57 may be pivotally connected to carriage 32, and should be manually or automatically retractable as shown in FIG. 1 when test cord 13 is outstide heating cavity 27 to avoid interference with an operator's change of test cord 13.

Measuring assembly 16 includes an angular displacement transducer (ADT) 51, weights 52 and 53, cable 54, and weights platform assembly 55. ADT 51 may be any transducer furnishing a signal that is accurately proportional to shaft angular displacement such as the Model 0600-0002 ADT from Trans-Tek Incorporated of Ellington Conn. A circular angular alignment scale 58 for initial angular alignment may be fixedly secured to ADT 51 by suitable means such as standoff bolts 59. A pulley 60 having a pointer 61 extending therefrom to permit accurate initial angular alignment as discussed below, is mounted to the shaft 62 of ADT 51. ADT 51 and its scale 58 and pulley 60 are all mounted to bracket 63, which is itself fixedly mounted to horizontal platform 33 such that measuring assembly 16 always moves inward and outward relative to heating cavity 27 in spaced relation with test cord 13.

Cable 54 extends from an anchor 64 attached to the closet side of grip 15, and passes around pulley 60 and through a bore 65 in horizontal platform 33 to weight 52, where it may be removably connected to weight 52 by an eyelet/hook combination. Pulley 60 is sized to receive cable 54 and rotate as cable 54 is laterally displaced.

Weights 52, 53 serve to maintain a minimal tension on test cord 13 and furnish whatever additional mechanical stress, if any, is desired during the test. Accordingly, weights 52, 53 may be of any desired weight and any number of weights may be combined, depending on test requirements.

Weights platform assembly 55 is designed to permit automatic addition and removal of weight 53 (and any additional weights). Weights platform assembly 55 includes weight platform 70, a suitable up/down drive motor 71 such as the screw drive Model SL 4013-001 Synchronous Linear Actuator manufactured by the Hurst Manufacturing Division, Emerson Electric Company of Princeton, Indiana, support column 72, guide rail 73, high and low platform stop switches 74, 75, and actuator 76.

Upon command from control 17, motor 71 raises or lowers weight platform 70 until actuator 76 engages position stop switches 74, 75, as corresponds to the commanded direction of operation. In the down or low position both weights are free of and not supported by weight platform 70, placing the mechanical stress of both weights 52 and 53 on test cord 13. In the up or high position, weight 53 is supported by weight platform 70, leaving only the tensioning weight 52 placed on test cord 13. The skilled artisan will now recognize that limited only by the height of support column 72, any number and combination of weights may be daisy chained to cable 54, and weight platform 70 controlled to insert or remove such weights from the load on test cord 13. Moreover, the weights, here shown as cylindrical with hooks and eyelets coaxially attached to and extending from each weight's top and bottom, may be configured so as to best facilitate such multiple daisy chained configuration.

Figure 3:
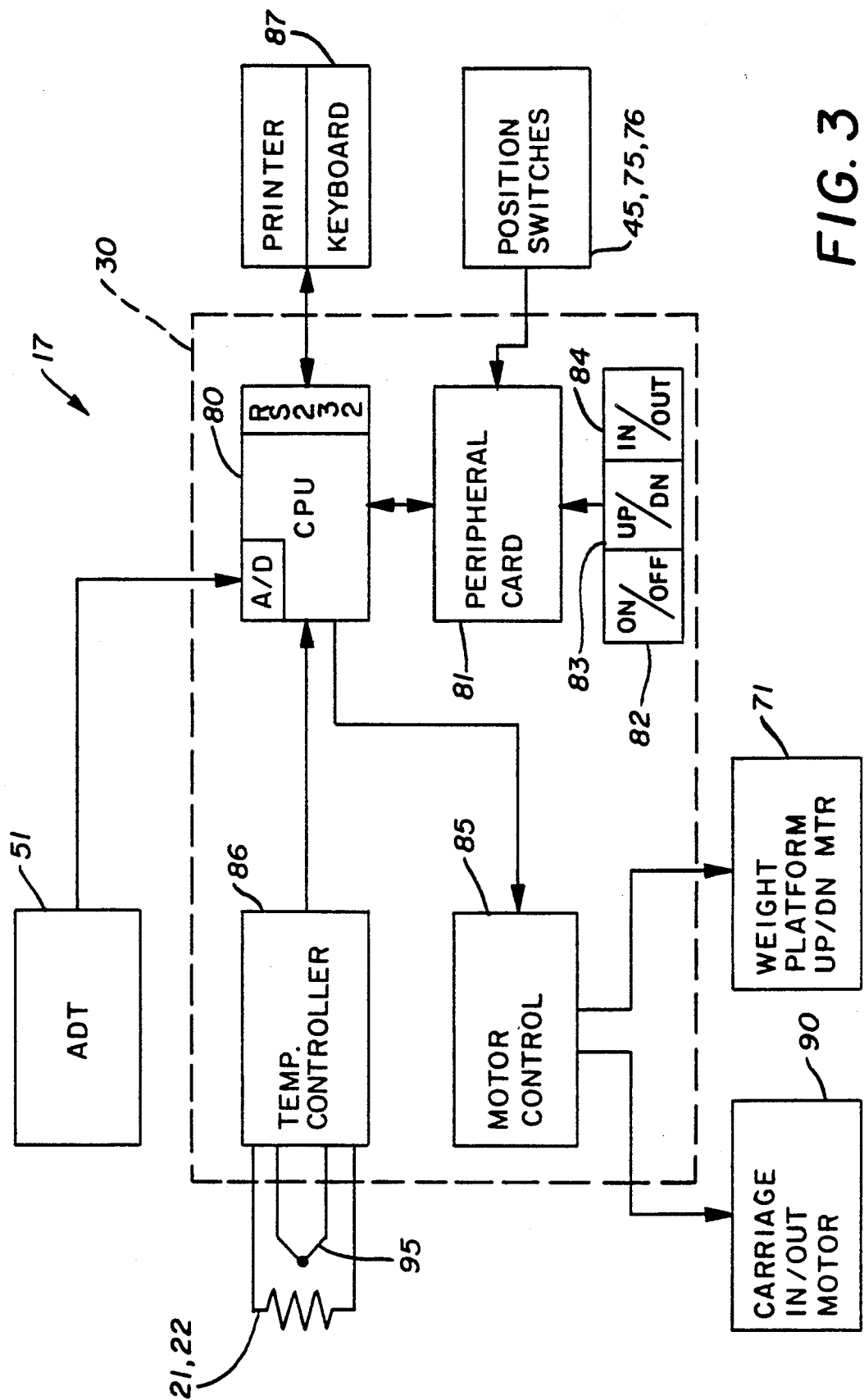
FIG. 3 is a block diagram of the control circuit for the exemplary device and method shown in FIG. 1.

FIG. 3 depicts a block diagram of control 17 and that connected to it. All components within the dashed-line box in FIG. 3 are found in or mounted upon housing 30. These components include microprocessor based central processing unit (CPU) 80, a CPU-supporting peripheral circuitry card 81, switches 82, 83 and 84, motor control 85, temperature controller 86, and printer/keyboard 87.

One CPU system suitable for use herein is that manufactured by Octagon Systems Corporation of Westminister Colo.; CPU 80 may be an Octagon Model SYS-2Z, including analog-to-digial (A/D) converters and to which conventional protocol input/output (I/O) devices may be connected; and, peripheral card 81 connected to CPU 80 may be an Octagon Model SUP-8 furnishing conventional TTL logic I/O lines, clock, back-up battery and reset features, among others.

Three conventional toggle switches 82, 83 and 84 may be mounted on the front of housing 30 to provide manual control of power, and weight platform and carriage position control, respectively. Switches 82, 83 and 84 are electrically connected to peripheral card 81 as are all position sensing switches 45, 75 and 76. Motor control 85 may be any conventional interface, such as a Model PB4 made by Gordos Arkansas Incorporated of Rogers Ark. for receiving the operational signals from CPU 80 and driving the appropriate motors 71 or 90.

Temperature controller 86, also mounted on the front face of housing 30, permits selection and accurate and precise control of the temperature within heating cavity 27, and is connected to CPU 80. Heating elements 21 and 22 receive their power from and are connected to temperature controller 86. A thermocouple 95 or other suitable accurate temperature sensor monitors the temperature within heating cavity 27 and provides to temperature controller 86 to which it is connected an output signal with one electrical characteristic proportional thereto. One temperature controller that has been found acceptable is the Model CN9111 Miniature Microprocessor Temperature Controller manufactured by Omega Engineering, Incorporated of Stamford, Conn.

A conventional computer terminal 87 including both a keyboard and printer, such as the Model 703 Data Terminal manufactured by Texas Instruments of Dallas, Tex., may be made part of control 17, connected to CPU 80 through a conventional RS-232 protocol communication interface, and carried for convenience by frame 20 below housing 30. While some form of signal entry keyboard is necessary at the location of device 10, the skilled artisan will understand that control 17 could be readily directly connected to another remote computer system for data logging and/or control.

ADT 51 may be electrically connected to CPU 80 through an on-board A/D converter, as shown in FIG 3.

Figure 4:
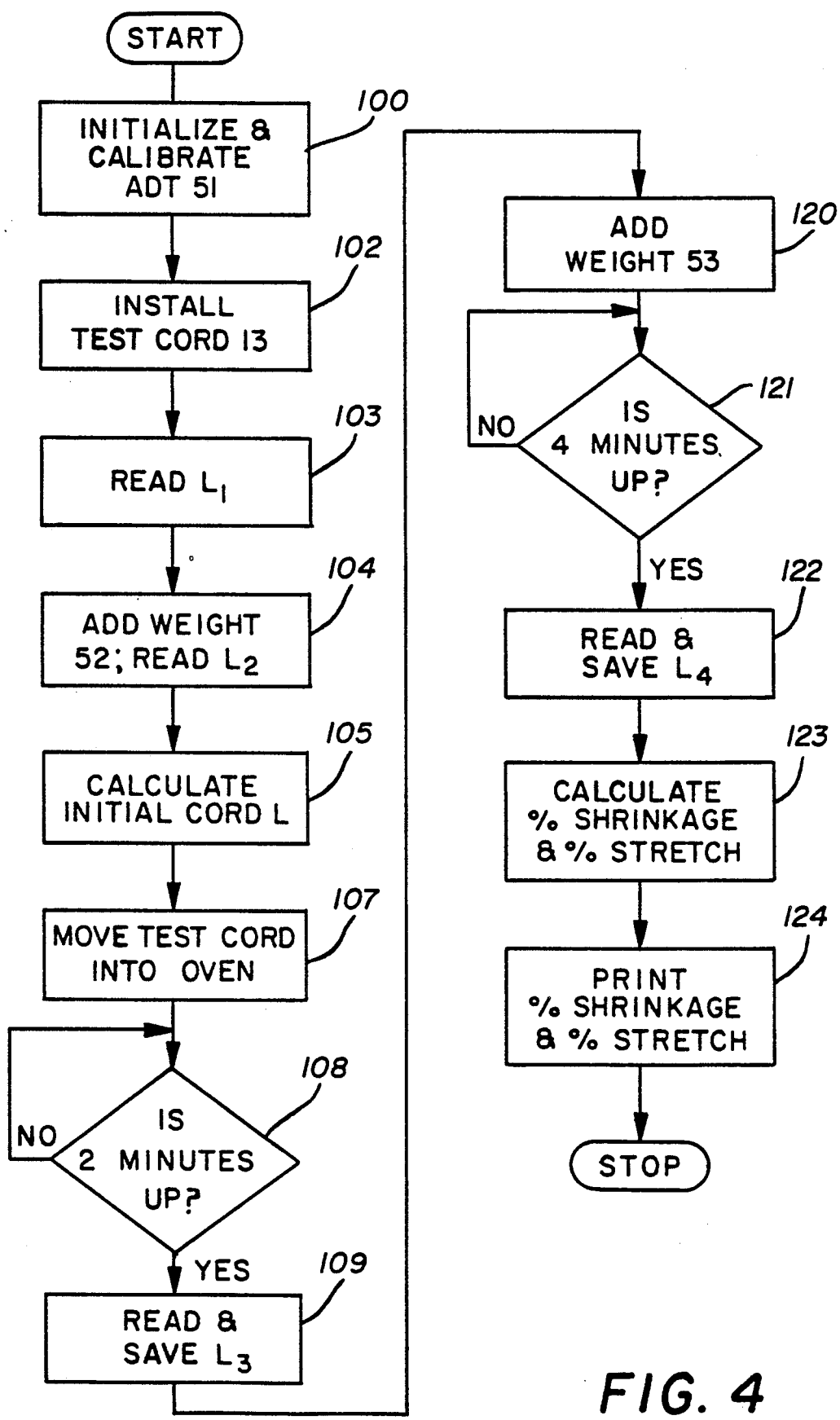
FIG. 4 is a flow chart of the operation of the exemplary device shown in FIG. 1.

The operation of device 10 may be most easily appreciated from the flow chart of FIG. 4. As indicated by box 100, the first step in a test routine begins with initialization of device 10 by insuring the power switch is on, both weights 52, 53 are detached from cable 54, weights platform 70 is in the up position, carriage 32 is in the out position, heat shield 57 is lowered, and temperature controller 86 is set to the desired test temperature setpoint.

A correlation is then obtained between the voltage magnitude output of ADT 51 and the linear displacement of test cord 13. This is accomplished by rotating pulley 60 until pointer 61 is aligned with a first reference mark on angular alignment scale 58, such as zero degrees. The enter key on keyboard 87 is pressed and CPU 80 reads the first voltage from ADT 51. This procedure is repeated with the pointer set to a second reference mark, such as sixty degrees. CPU 80 then calculates a calibration factor in inches per volt by subtracting the later read voltage from the first read voltage and dividing the difference by a constant to convert the angular distance of pulley 69 to a linear dimension.

Next test cord 13 is installed in grips 14, 15 and an accurate measurement of its initial length is obtained. The thumbwheel screw 47 on grip 14 is loosened, and one end of test cord 13 passed between jaws 40 and 41 down the channel between legs 38 and 39, and, if necessary, directed outward around offset 50, whereupon thumbwheel screw 47 is tightened to clamp test cord 13 between jaws 40 and 41.

In order to insure test cord 13 starts with a known distance, grip 15 is laterally moved to a preselected distance from grip 14 before the free end of test cord 13 is attached to it. This may be most conveniently achieved by use of an alignment stop 101 shown in FIG. 1. Alignment stop 101 is pivotally connected to the top of channel block 37 so that it may rotate between the non-interference position shown in FIG. 1 at a right angle to the longitudinal axis of channel block 37, to an alignment position parallel to such axis. Grip 15 may be slid away from grip 14 until it engages alignment stop 101 and held in that position while test cord 13 is pulled taut and its free end is connected to grip 15 as was done for grip 14. By appropriately selecting the length of alignment stop 101, the initial length of test cord 13, referred to as length $L_1$, may be made to be whatever is desired, such as the eight inches we have found convenient.

Once test cord 13 is secured to grip 14, the enter key is pressed on keyboard 87 and CPU reads $L_1$, an uncorrected "0%" stretch length for test cord 13, as depicted in step 103. Next, alignment stop 101 is returned to its noninterference position, heat shield 57 is raised, tension weight 52 is hooked to cable 54, and the enter key is pressed. CPU 80 then completes step 104 by reading $L_2$, and calculates the actual initial length of test cord 13. In the present instance, the actual length equals eight inches plus the difference between the final and original lengths $(8+L_2-L_1)$.

Steps 100-105, inclusive, may be viewed as necessary setup, initialization and calibration procedures. Step 107, where CPU 80 actuates motor 90 to move carriage 32 inward until the entire length of test cord 13 is enclosed within heating cavity 27, begins the actual test.

Once test cord 13 has been heated for two minutes at the preselected temperature setpoint (step 108), cord length (now called $L_3$) is again measured (step 109) and stored in memory. In step 120 CPU 80 actuates drive 71 to lower weights platformm 70, adding weight 53 to cable 54. After a four minute delay (step 121), cord length (now called $L_4$) is again measured and stored in memory (step 122).

Upon conclusion of both tests, percent shrinkage and stretch may be calculated (step 123) and printed (step 124). Percent shrinkage is equal to $[(L_3-L_2)/\text{actual initial length}]\times 100$ where the actual initial length is $8+(L_2-L_1)$. Percent stretch is equal to $[(L_4-L_2)/(8+(L_2-L_3))]\times 100$.

At the conclusion of the test routine CPU 80 actuates motor 90 to move carriage 32 outward and actuates drive 71 to raise weights platform 70. Test cord 13 may be removed from grips 14, 15 and replaced with another cord to be tested, or power switch 82 turned off.

The presence of microprocessor operated control 17 permits much additional data collection, storage and analysis beyond final percent shrinkage and percent stretch. For example, CPU 80 could read test cord length periodically throughout a test cycle and store and analyze such data. Moreover, the skilled artisan will understand that device 10 may be used to implement a wide variety of test protocols. For example, in the embodiment described herein, the temperature of heating cavity 27 is maintained constant throughout both shrinkage and stretch tests. However, the temperature of heating cavity 27 could be readily varied during the test periods as desired. Other parameters of the test routine, such as weights and time delays, also may be readily varied.

Inasmuch as the present invention is subject to many variations, modifications and changes in detail, a number of which have been expressly stated herein, it is intended that all matter described throughout this entire specification or shown in the accompanying drawings be interpreted as illustrative and not in a limiting sense. It should thus be evident that a device constructed and method performed according to the concept of the present invention, and reasonably equivalent thereto, will accomplish the objects of the present invention and otherwise substantially improve the art of determining dimensional change in a material under thermomechanical stress.

We claim:

1. A device for determining dimensional change in a material under thermomechanical stress, comprising:
    chamber means for receiving and controlling the temperature of a preselected length of the material;
    grip means for holding said preselected length of the material, selectively positioning the entire said preselected length of the material within said chamber means and selectively retracting the entire said preselected length of material from said chamber means; and,
    means for measuring changes in said preselected length of material.

2. A device for determining dimensional change in a under thermomechanical stress, as set forth in claim 1, further including control means for automatically, selectively moving said grip means such that the material held by said grip means is positioned entirely within said chamber means, selectively moving said grip means such that the material held by said grip means within said chamber means is retracted from said chamber means, operating said chamber means for a preselected timed cycle, monitoring changes in said preselected length of material, and calculating the dimensional change.

3. A device for determining dimensional change in a material under thermomechanical stress, as set forth in claim 2, wherein said chamber means includes temperature control means for controlling the temperature within said chamberr means.

4. A device for determining dimensional change in a material under thermomechanical stress, as set forth in claim 1, wherein said chamber means is an oven including a heating cavity, said grip means includes a plurality of legs for grasping an end of said length of material, and the end of said legs grasping said length of material is positionable within said heating cavity.

5. A device for determining dimensional change in a material under thermomechanical stress, comprising:
    oven means for receiving and controlling the temperature of a preselected length of the material, said oven means including a heating cavity;
    grip means for holding and selectively positioning the entire said preselected length of the material within said oven means, said grip means including a plurality of legs for grasping an end of said length of material, and the end of said legs grasping said length of material positionable within said heating cavity;
    means for measuring changes in said preselected length of material, said means for measuring changes including transducer means for measuring dimensional changes, said transducer means in operative association with said grip means, and weight means connected to said grip means for selectively applying mechanical stress to the material; and,
    control means for automatically, selectively controlling the connection of said weight means to said grip means.

6. A device for determining dimensional change in a material under thermomechanical stress, as set forth in claim 5, wherein said means for measuring changes includes platform means in operative association with said weight means for connecting and disconnecting said weight means from said grip means.

7. A device for determining dimensional change in a material under thermomechanical stress, as set forth in claim 6, wherein the material is tire cord, and said weight means is a plurality of weights.

8. A grip for anchoring a length of material whose change in length under thermomechanical stress is to be determined by insertion into a temperature controlled chamber having a long, narrow heating cavity therein, the grip including a first portion for grasping one end of the material and a second portion for operationally engaging the first portion, the improvement comprising configuring the first portion such that the entire length of material may be selectively, removably inserted within the heating cavity.

9. A grip for anchoring a length of material, as set forth in claim 8, wherein said first portion includes a plurality of legs having jaws for grasping the length of material, eachh said leg having a bore therein to minimize its mass.

10. A grip for anchoring a length of material, as set forth in claim 9, wherein one said leg includes offset means for retaining the end of the length of material extending beyond said jaws.

11. A method for determining dimensional change in a material under thermomechanical stress, comprising the steps of:
   inserting a preselected length of the material into grips;
   positioning selectively, removably the entire said preselected length of the material including the portion of said grips holding the material within an oven;
   controlling the temperature of said preselected length of the material in said oven; and,
   measuring changes in said preselected length of material.

12. A method for determining dimensional change in a material under thermomechanical stress, as set forth in claim 11, further including the steps of automatically, selectively moving said grips such that the material held by said grips is positioned entirely within said oven, and operating said oven for a preselected timed cycle.

13. A method for determining dimensional change in a material under thermomechanical stress, as set forth in claim 11, further including the step of selectively applying mechanical stress to the material.

* * * * *